United States Patent [19]

Berndt

[11] Patent Number: 5,338,535
[45] Date of Patent: Aug. 16, 1994

[54] NON-AQUEOUS LIQUID POWDER

[75] Inventor: Dieter R. Berndt, Allenwood, N.J.

[73] Assignee: The Safe & Dry Company, Inc., Spring Lake, N.J.

[21] Appl. No.: 995,795

[22] Filed: Dec. 23, 1992

Related U.S. Application Data

[63] Continuation-in-part of Ser. No. 771,217, Oct. 4, 1991, abandoned.

[51] Int. Cl.$^5$ ............................................. A61K 7/02
[52] U.S. Cl. ...................... 424/69; 424/401; 514/865; 514/952; 514/63; 514/778
[58] Field of Search ............... 424/401, 69; 514/778, 514/865, 952, 63

[56] References Cited

U.S. PATENT DOCUMENTS

| | | | |
|---|---|---|---|
| 4,857,307 | 8/1989 | Suss | 424/401 |
| 4,913,896 | 4/1990 | Harvey | 424/401 |
| 4,921,701 | 5/1990 | Blehm Blank | 424/401 |
| 4,983,388 | 1/1991 | Kuwata | 424/401 |
| 5,069,897 | 12/1991 | Orr | 424/401 |

OTHER PUBLICATIONS

Gennaro (1985) Renington's Pharmaceutical Sciences, Mack Publishing, pp. 774–775, 1318.

Primary Examiner—Paul R. Michl
Assistant Examiner—Raj Bawa
Attorney, Agent, or Firm—Henry D. Coleman; R. Neil Sudol

[57] ABSTRACT

This invention discloses a liquid body powder which is applied as a lotion or a cream and which then evaporates to a powder. By applying it as a lotion or cream, the cracks and pores of the skin are filled. By virtue of the volatility of the cyclic silicone fluid containing delivery vehicle and its evaporation, a powder results which leaves no greasy residue on the skin. The liquid powder according to the present invention comprises a purified starch powder mixed with a volatile cyclomethicone silicone fluid, preferably in equal amounts by weight.

25 Claims, No Drawings

NON-AQUEOUS LIQUID POWDER

RELATED APPLICATIONS

This application is a continuation-in-part application of U.S. Ser. No. 07/771,217, entitled "Non-Aqueous Liquid Powder", filed Oct. 4, 1991, now abandoned.

FIELD OF THE INVENTION

This invention relates to a delivery system of body dusting powders and, more particularly, to a unique delivery system for more effectively and thoroughly applying a body powder to the skin's surface while at the same time eliminating powder toxicity due to the inclusion of talc and/or anti-caking agents. Compositions according to the present invention are substantially nontoxic and biodegradable. Preferred compositions according to the present invention are hypoallergenic and are comprised of primarily natural ingredients.

BACKGROUND OF THE INVENTION

As is well known and understood, a great many of the dusting powders (including baby and body powders, in general, on the market today) contain varying amounts of talc. It has also been publicized, however, that talc has been determined to be a potential cause of pulmonary disorder. At least in part because of this danger—and additionally the possibility that talc powders present an inhalation danger as well as a potential danger by virtue of their being able to be absorbed into the body via cracked, open skin—more and more manufacturers began to eliminate talc powders from their product lines. Talc has been replaced with other powders employing corn starch or rice starch. Those manufacturers using corn starch or rice starch, however, employ calcium phosphates (e.g. calcium triphosphate) as anti-caking and anti-clustering agents. The problem with these formulations is the fact that the calcium phosphates tend to be serious mucous membrane irritants—to the extent that when they are employed to keep the corn starch or rice starch from clustering, the manufacturer often carries a warning on the product label. It is recommended that these powder products be kept away from the face of a child being treated with the powder to minimize inhalation of the powder and the possible breathing difficulties which may result.

Thus, while the body powder manufacturers have succeeded at least to some extent in eliminating talc from the powder market, the alternative product incorporates deleterious agents by necessity, which have been suggested to be irritating and harmful to mucous membranes and the upper respiratory tract as well as the eyes and skin.

The initial investigation of liquid powder mixtures included micro-milling (below about 10 microns) polysaccaride particles such as starches in conjunction with alcohols and ethers. Starch in the above form is white powder, and the naked eye can detect little difference between the various starches extracted from different plants. Numerous percent composition mixtures were made ranging from 20–80% starch and 80–20% alcohol and/or ether, respectively. However, even though these mixtures provided the simple basis for a liquid powder product they were undesirable for a number of reasons, many of them related to the inadequacies of the delivery vehicle.

The above-described material compositions resulted in product deficiencies which brought about the need to investigate an alternative to the alcohols and ethers.

Organosilicones are not found in nature and must be prepared synthetically. The ultimate starting material is sand (silicon dioxide) or other inorganic silicates, which make up 75% of the Earth's crust. The organosilicones were first synthesized in 1863 by Friedel and Crafts, who first prepared tetraethylsilane. In the following years, although many other derivatives were synthesized, it was not until the 1940's that widespread interest in organosilicon chemistry emerged.

Silicon is a relatively electropositive element that forms polar covalent bonds with carbon and other elements, including the halogens, nitrogen and oxygen. The strength and reactivity of silicon depend on the relative electronegativity of the element to which the silicone will be covalently bound. The polysilanes upon controlled hydrolysis readily form the polysiloxanes. These cyclic and linear polymers are commercially known as silicones. The cylic siloxanes are used in the present invention as delivery vehicles for body powders to provide compositions with unique characteristics.

OBJECTS OF THE INVENTION

It is an object of the present invention, therefore, to provide a body powder in which all the irritants presently employed in current manufactures are eliminated.

It is another object of the invention to provide such a body powder which can be used by adults as well, and which is bio-degradable, bio-erodable and environmentally compatible.

It is a further object of the invention to provide a dusting powder, including a baby or body powder without talc, and without any anti-caking chemicals which introduce inhalation problems and skin irritation.

It is yet an additional object of the invention to provide a unique delivery system to more effectively and thoroughly apply baby powder to the skin's surface in a manner which completely eliminates any dangers from inhaling toxic powder particles.

It is still a further object of the present invention to provide liquid dusting powder compositions which can be used to deliver active agents intended to produce a pharmacological or biological effect.

SUMMARY OF THE INVENTION

As will become clear from the following description, the present invention describes a dusting body powder which is applied as a lotion, and which then evaporates to leave behind a powder. By applying it as a lotion, the danger of inhaling any toxic powder particle is eliminated. By applying it as a lotion, furthermore, all cracks and pores of the skin are filled, as it can reach hard-to-get-at crevices so as to ensure better product coverage. By virtue of its evaporation to a powder, no greasy residue is left on the skin.

DETAILED DESCRIPTION OF THE INVENTION

These and other features of the invention arise from the use of a delivery system in which a starch powder, preferably purified, is added and mixed with such cyclomethicone silicone fluids as decamethylcyclopentasiloxane, octamethylcyclotetrasiloxane or other volatile cyclosiloxanes. In general, the amount of cyclosiloxane included in compositions according to the present invention ranges from about 25% to about 75% or more by weight, preferably about 25% to about 50% by weight and most preferably about 35% by weight. The amount of starch which is generally included in compositions according to the present invention ranges from about 25% to about 75% by weight, preferably about 50% to about 75%, most preferably about 65% by weight. Of course, one of ordinary skill in the art will recognize that the inclusion of amounts of cyclosiloxane and/or starch outside of these ratios may also be effective, depending upon the characteristics of further additives which may be used and the ultimate characteristics of the final compositions desired. For example, the inclusion of an alternative powder or a volatility enhancer which acts like starch in compositions according to the present invention may reduce the need of starch to an amount which is significantly less than the above-disclosed weight ratios. In other instances, it may be advisable to include the volatile cyclosiloxane in an amount which is substantially less than about 25% by weight of the composition, especially when other delivery vehicles or certain film-forming agents are also included in the compositions. It is recognized that the above-described weight ratios should serve to guide, not limit, the formulation of compositions according to the present invention.

Below about 25% by weight of the composition, the amount of cyclosiloxane may be too limited to provide the exceptional delivery characteristics that generally characterize the use of volatile cyclosiloxanes in this invention. When the amount of starch is below about 25% by weight of the composition, this may reduce the volatility of the cyclosiloxane and produce a "watery" product. Above about 70–75% by weight starch, the starch tends to clump together into an undesirable paste-like consistency.

The weight ratio of cyclosiloxane to starch in compositions according to the present invention may vary within the above-described range, but cyclosiloxane and starch is preferably included in about a 1:2 weight ratio, in certain instances, a 1:1 weight ratio, depending upon other additives which are included in the composition. One of ordinary skill in the art will understand to vary the weight ratio of cyclosiloxane and starch to maximize the properties desired for a particular effect, recognizing that the starch is included for its benefit as a powder and its ability to enhance volatility or evaporation of the cyclosiloxane from the skin surface and the cyclosiloxane is included for its delivery characteristics, its volatility and its bio-erodability and biodegradability.

The preferred liquid powder product which contains only volatile cyclomethicone and starch powder ranges from about 60% to about 70% by weight starch, most preferably about 65% and about 30% to about 40% by weight volatile cyclomethicone, most preferably about 35%.

The following represents a representative series of liquid body powders according to the present invention:

| Starch* | Cyclomethicone* | Consistency and Description |
|---|---|---|
| 44 | 56 | low viscosity liquid |
| 50 | 50 | medium viscosity liquid |
| 58 | 42 | high viscosity liquid |
| 61 | 39 | low visocity cream |
| 64 | 36 | medium viscosity cream |
| 67 | 33 | high viscosity cream |

*in percent by weight.

It is an unexpected result that the volatile cyclosiloxanes may be used as delivery vehicles for the non-aqueous body powders of the present invention. Although the cyclosiloxanes which are included in the present invention are known to be somewhat volatile, the volatility is generally limited at room temperature, with boiling points ranging from about 175° F. to over 200° F. Thus, although evaporation of a volatile agent from the skin would be expected to ultimately occur (usually, at least about 30 minutes after being delivered to a surface such as the skin), the volatility of the cyclosiloxanes, without the inclusion of a volatility enhancer such as starch, is insufficient to be as useful as the compositions according to the present invention. As used herein the term "cyclosiloxane" and "cyclomethicone" are used interchangeably.

It has surprisingly been discovered that the volatile cyclosiloxanes will evaporate quickly from the surface of the skin when formulated with starch, according to the present invention. While not being limited by way of theory, it is believed that this unexpected result may occur because the inclusion of the starch may serve to disperse the cyclosiloxane delivery vehicle, thus maximizing surface area to which the cyclosiloxanes are exposed. It is believed that the dispersion action of the starch powders within the cyclomethicone delivery vehicle increases up to about 5 times the evaporation of the formulated cyclomethicone relative to non-dispersed cyclomethicone. The result is that the evaporation of the cyclosiloxane delivery vehicle from the surface of the skin is unexpectedly enhanced. In essence, the cyclomethicone and starch work to produce a hand-in-glove system- the cyclomethicone evaporates faster in the starch powder and the starch is more easily delivered to the surface of the skin as a non-dusting powder.

It is another feature of the present invention to include a volatile lower alcohol such as methanol, ethanol or isopropanol to promote the volatility of the cyclomethicone delivery vehicle. These volatile alcohols can be mixed in various ratios from as little as about 0.1% to about 30% by weight of the formulation to provide successful compounding of the liquid body powder of the present invention. The inclusion of ethanol or isopropanol as the volatile alcohol is clearly preferred with ethanol being most preferred. Benefits of including a volatile alcohol in compositions according to the present invention include achieving a cooling sensation on the body via the increased volatility and enhanced delivery of the powder in dry form. In addition, as will be explained hereinbelow, the inclusion of a lower alcohol may make the compositions easier to formulate. The following comparisons are noted for the evaporation rates of cyclosiloxanes and the lower alcohols used in the instant invention for purposes of enhancing evaporation of cyclomethicone.

| Component Cyclosiloxane or Alcohol | Evaporation Rate |
|---|---|
| Decamethylcyclopentasiloxane | 3.4 mg/hr/cm$^2$ |
| Octamethylcyclotetrasiloxane | 14 mg/cm$^2$ |
| Ethyl Alcohol | 24 mg/hr/cm$^2$ |
| Methyl Alcohol | 35 mg/hr/cm$^2$ |

-continued

| Component Cyclosiloxane or Alcohol | Evaporation Rate |
|---|---|
| Isopropyl Alohol | 18 mg/hr/cm$^2$ |

The volatile alcohols are readily soluble in the cyclomethicone provided that water is substantially removed from the formulation. The inclusion of at least one volatile alcohol will substantially enhance the evaporation rate of the cyclomethicone. For example, the following mixtures yield the indicated evaporation rates:

| Component Cyclosiloxane/Alcohol | Evaporation Rate |
|---|---|
| Pentamer/Ethanol (50/50 by weight) | 15.5 mg/hr/cm$^2$ |
| Pentamer/Ethanol (80/20 by weight) | 7.2 mg/hr/cm$^2$ |
| Pentamer/Isopropanol (50/50 by weight) | 10.6 mg/hr/cm$^2$ |
| Pentamer/Isopropanol (80/20 by weight) | 4.2 mg/hr/cm$^2$ |

Although numerous percent mixtures can be obtained for the materials containing cyclosiloxane and volatile alcohol, the above-described mixtures are presented to show their combined performance to enhance evaporation of the cyclomethicones. While not being limited by way of theory, it is believed that the volatile alcohols function to enhance the evaporation rate of the cyclomethicones through their solubility, by functioning as integral active chemical dispersants to increase volatility of the cyclomethicones. This contrasts with the action of the starches which are believed to function as static mechanical surface area dispersants.

In addition to enhancing the volatility of the cyclomethicones, the inclusion of effective amounts of at least one lower alcohol will help to lower the freezing point of the cyclomethicones, in particular, octamethylcyclotetrasiloxane, which has a freezing point of 11° C. and a five-fold greater volatility than its pentameric homologue, decamethylcyclopentasiloxane, which has a freezing point of −40° C. Thus, another feature of the instant invention relates to the inclusion of effective amounts of at least one lower alcohol selected from among ethanol, methanol and isopropanol added to cyclomethicone-containing compositions according to the present invention, preferably those compositions containing octamethylcyclotetrasiloxane, in order to lower the freezing point of the cyclomethicone. The result is a formulation which is easier to work with, and will provide greater low temperature storage stability. In order to influence the freezing point of the cyclomethicone, the lower alcohol is preferably added to the cyclomethicone and starch in at least about 5% by weight of the composition, and preferably at least about 10% to about 30% by weight of the composition. In most preferred compositions according to this aspect of the present invention, an amount of ethanol ranging from about 10% to about 30% by weight of the composition is added for this intended purpose.

In addition to cyclosiloxane and starch (and, in certain embodiments, a volatile alcohol such as, preferably, isopropanol or ethanol), compositions according to the present invention may also include both inert and active agents, for example, fragrances and coloring additives, film formers such as petroleum jelly and mineral oil and medicinals such as camphor, zinc oxide and sulfur, among others, including vitamins such as vitamin A, D and E, in amounts ranging from about 0.1% to about 50% by weight of the final compositions. In the case of fragrances or coloring agents, these additives are generally included in effective amounts, i.e., generally less than about 1% by weight of the final powder product.

In addition, the inclusion of active agents, such as anti-fungal agents (and in particular, athlete's foot compositions) and antimicrobial agents is a further aspect according to the present invention. One of ordinary skill in the art without undue experimentation will recognize to include a particular agent in compositions according to the present invention for the agent's known benefit in amounts which would produce an intended result without substantially impacting the overall favorable characteristics of compositions according to the present invention.

The following active agents, among others, may be included in the compositions according to the present invention to produce a wide variety of pharmacologically active body powders:

Anti-Fungals
  Terconazole
  Econozole
  Hamycin
  Mepartricin
Anibiotics/Anti-Bacterials
  Nifutoinol
  Miloxacin
  Sulfadiazine
  Thiazolsulfone
  Cefadroxil
Anti-Inflammatory
  Fenoprofen
  Acemeticin
  Acetylsalicylic acid
  Salicetamide
Anti-Puritic
  Camphor
  Menthol
  Risocaine
  Phenol
  Dichlorisone
Anti-Acne
  Benzoyl Peroxide
  Dichloroacetic Acid
  Salicylic Acid
  Tetroquinone
Hemostatic
  Algin
  Alginic Acid
  Ellagic Acid
  Vasopressin
  Thrombin
  Cephalin
Anti-Histaminic
  Dimethindene
  Bamipine
  Triprolidine
  Setastine
  Promethazine These agents are generally included in compositions according to the present invention in amounts ranging from about 0.01% to about 20% by weight, depending upon the activity of the agent included and the intended use of the composition.

In a specific embodiment of the present invention, for example, purified corn starch or rice starch can be obtained from various supply houses in readily available quantities, and mixed in a 1:1 ratio by weight—as in a blending process where the cyclomethicone silicone fluid is slowly added to the starch powder and blended and milled to a free-flowing lotion. When carrying this out in a commercial blender, as at room temperature, a liquid-powder lotion of 1,000# can be produced in about 75 minutes, more or less, and then filled in any appropriate manner to plastic squeeze-bottles, vials, or other such containers.

When using decamethylcyclopentasiloxane, octamethlcyclotetrasiloxane and other cyclosiloxane as the cyclomethicone silicone fluid, the liquid-powder lotion may be applied to the body as a moist white cream. After being rubbed in place, the composition usually becomes clear and almost invisible while its evaporation proceeds, leaving only the purified starch behind. The compositions thus may be formulated to deposit pure starch powder in the cracks and crevices of the skin, without leaving any irritants, toxic particles or liquid residues which occur in the prior art compositions.

The liquid body powder of the present invention may be used as an adult liquid body powder, as a replacement for traditional baby powder, as a liquid feminine hygiene powder or alternatively as a liquid medicated powder for treating athlete's foot, "jock itch", prickly heat, skin irritation, among other uses.

The following examples are provided to illustrate the present invention and should not be construed to limit the scope of the invention of the present application in any way.

EXAMPLE 1

Pure Hypo-allergenic Liquid Body Powder

Materials

| Decamethylcyclopentasiloxane | 2,500 grams |
|---|---|
| Pure Cornstarch | 2,500 grams |

Method of Preparation

A mixture of 2,500 grams of each of the above materials (the cyclosiloxanes may be obtained from the Dow Chemical Corp. or the General Electric Company and the starch materials may be obtained from National Starch, Inc.) was slowly fed into a continuous-phase colloid mill (Bakker 1200) with a mesh setting at 2-5 microns. A milling cycle of 2 hours was sufficient at which point all starch particles were within the 2-5 micron size range.

The above mixture was then transferred into a closed chamber where it was degassed under vacuum for 2 hours and allowed to settle for an additional 10 hours to produce a liquid body powder.

Resulting Product Specification

The above described liquid body powder had the following characteristics:

| 1. Viscosity: | 65 cps |
|---|---|
| 2. Evaporation Rate: | 21 mg/hr/cm$^2$ |
| 3. Temperature Stability: | $-40°$ C. to 60° C. |
| 4. Estimated Shelf Life: | 60 Months (bottled) |

EXAMPLE 2

Liquid Body Powder for Dry Skin

Materials

| Decamethylcyclopentasiloxane | 2,250 grams |
|---|---|
| Pure Cornstarch | 2,500 grams |
| White Petroleum Jelly (Petrolatum USP) | 250 grams |
| Total | 5,000 grams |

Method of Preparation

The petroleum jelly was heated to 90° C. and then added slowly to the cyclosiloxane. This mixture was then passed through a continuous phase colloid mill, cycled for 2 hours (at a mesh setting of 1 micron) and cooled to room temperature.

The resultant cloudy colloidal mixture was then added to the cornstarch to form a mixture which was put through the colloid mill and cycled for 2 hours (at a mesh setting of 2-5 microns).

The mixture was then degassed as above and allowed to settle for 10-12 hours before it was ready for packaging.

Resulting Product Specification

The above described liquid body powder had the following characteristics:

| 1. Viscosity: | 90 cps |
|---|---|
| 2. Evaporation Rate: | 8 mg/hr/cm$^2$ |
| 3. Temperature Stability: | 10° C. to 40° C. |
| 4. Estimated Shelf Life: | 60 Months (bottled) |

EXAMPLE 3

Liquid Baby Powder

Materials

| Decamethylcyclopentasiloxane | 1,750 grams |
|---|---|
| Pure Cornstarch | 2,500 grams |
| White Petroleum Jelly (Petrolatum USP) | 500 grams |
| Mineral Oil USP | 250 grams |
| Total | 5,000 grams |

Method of Preparation

The petroleum jelly and mineral oil were mixed and heated to 90° C. and then added slowly to the cyclosiloxane. This mixture was then passed through a continuous phase colloid mill, cycled for 2 hours (at a mesh setting of 1 micron) and allowed to cool down to room temperature.

The resultant cloudy colloidal mixture was then added to the cornstarch to form a mixture which was put through the colloid mill and allowed to cycle for 2 hours (at a mesh setting of 2-5 microns).

The mixture was then degassed as above and allowed to settle for 10-12 hours before it was ready for packaging.

Resulting Product Specification

The above described liquid baby powder had the following characteristics:

| | |
|---|---|
| 1. Viscosity: | 85 cps |
| 2. Evaporation Rate: | 9.5 mg/hr/cm² |
| 3. Temperature Stability: | −20° C. to 60° C. |
| 4. Estimated Shelf Life: | 60 Months (bottled) |

EXAMPLE 4

Liquid Medicated Powder

Materials

| | |
|---|---|
| Decamethylcyclopentasiloxane | 2,500 grams |
| Rice Starch | 1,750 grams |
| Zinc Oxide | 500 grams |
| Camphor | 250 grams |
| Total | 5,000 grams |

Method of preparation

The above mixture was ball-milled for a period of 6 hours (in compositions containing inorganic materials, ball milling is preferred over the colloid milling process because it can best disperse and grind the inorganic materials such as the zinc oxide).

The mixture was then tested for particulate size to make certain the size was under 5 microns and then further milled for another 2 hours to ensure a particulate size of less than about 5 microns.

The mixture was then degassed as above and allowed to settle for about 6 hours before packaging.

Resulting Product Specification

The above described liquid medicated powder has the following characteristics:

| | |
|---|---|
| 1. Viscosity: | 65 cps |
| 2. Evaporation Rate: | 23 mg/hr/cm² |
| 3. Temperature Stability: | −40° C. to 60° C. |
| 4. Estimated Shelf Life: | 60 Months (bottled) |

EXAMPLE 5

Liquid Medicated Powder

Materials

| | |
|---|---|
| Decamethylcyclopentasiloxane | 1,250 grams |
| Octamethylcyclotetrasiloxane | 1,250 grams |
| Rice Starch | 1,750 grams |
| Zinc Oxide | 500 grams |
| Camphor | 250 grams |
| Total | 5,000 grams |

Method of Preparation

The above mixture was ball-milled for a period of 6 hours and then tested for particulate size. After testing, the mixture was further milled for a period of 2 hours, thus ensuring a particle size of less than 5 microns. The mixture was thereafter degassed and allowed to settle for 6 hours before packaging.

Resulting Product Specification

The above described liquid medicated powder had the following characteristics:

| | |
|---|---|
| 1. Viscosity: | 65 cps |
| 2. Evaporation Rate: | 23 mg/hr/cm² |
| 3. Temperature Stability: | 10° C. to 60° C. |
| 4. Estimated Shelf Life: | 60 Months (bottled) |

EXAMPLE 6

Liquid Body Powder

Materials

| | |
|---|---|
| Decamethylcyclopentasiloxane | 1,750 grams |
| Pure Cornstarch | 2,500 grams |
| White Petroleum Jelly (Petrolatum USP) | 500 grams |
| Mineral Oil USP | 250 grams |
| Total | 5,000 grams |

Method of Preparation

The petroleum jelly and mineral oil were mixed and heated to 90° C. and then added slowly to the cyclosiloxane. This mixture was then passed through a continuous phase colloid mill and cycled for 2 hours (at a mesh setting of 1 micron) and cooled to room temperature.

The resultant transluscent colloidal mixture was then added to the cornstarch to form a mixture which was passed through the colloid mill and cycled for 2 hours (at a mesh setting of 2–5 microns).

The mixture was then degassed as above and allowed to settle for 10–12 hours before packaging.

Resulting Product Specification

The above described liquid body powder has the following characteristics:

| | |
|---|---|
| 1. Viscosity: | 80 cps |
| 2. Evaporation Rate: | 13.5 mg/hr/cm² |
| 3. Temperature Stability: | 12° C. to 60° C. |
| 4. Estimated Shelf Life: | 60 Months (bottled) |

EXAMPLE 7

Sore Muscle Rub Powder Lotion

Materials: In Percent by Weight

| | |
|---|---|
| Cyclomethicone | 35% |
| Starch | 55% |
| Menthol | 5% |
| Camphor | 5% |
| Total | 100% |

Method of Preparation

The above components are thoroughly mixed and the resulting mixture is slowly fed into a continuous-phase colloid mill with a mesh setting at 2–5 microns. A milling cycle of 2 hours is utilized and the resulting product is tested for particulate size. Milling is continued until all starch particles are within the 2–5 micron size range.

The above mixture is thereafter transferred into a closed chamber where it is degassed under vacuum for about 2 hours and allowed to settle for an additional period to produce a liquid body powder.

EXAMPLE 8

Athlete's Foot Powder Lotion

Materials: In Percent by Weight

| | |
|---|---|
| Cyclomethicone | 35% |
| Starch | 40% |
| Sulfur | 10% |
| Zinc Oxide | 10% |
| Terconazole | 5% |
| Total | 100% |

Method of Preparation

The above components are thoroughly mixed and the resulting mixture is slowly fed into a continuous-phase colloid mill with a mesh setting at 2-5 microns. A milling cycle of 2 hours is utilized and the resulting product is tested for particulate size. Milling is continued until all starch particles are within the 2-5 micron size range.

The above mixture is thereafter transferred into a closed chamber where it is degassed under vacuum for about 2 hours and allowed to settle for an additional period of time to produce a liquid body powder.

EXAMPLE 9

Anti-Ache Powder Lotion

Materials: In Percent by Weight

| | |
|---|---|
| Cyclomethicone | 35% |
| Starch | 45% |
| Sulfur | 15% |
| Tetroquinone | 5% |
| Total | 100% |

Method of Preparation

The above components are thoroughly mixed and the resulting mixture is slowly fed into a continuous-phase colloid mill with a mesh setting at 2-5 microns. A milling cycle of 2 hours is utilized and the resulting product is tested for particulate size. Milling is continued until all starch particles are within the 2-5 micron size range.

The above mixture is thereafter transferred into a closed chamber where it is degassed under vacuum for 2 hours and allowed to settle for an additional period of time to produce a liquid body powder.

EXAMPLE 10

Medicated Baby Powder Lotion

Materials: In Percent by Weight

| | |
|---|---|
| Cyclomethicone | 35% |
| Starch | 50% |
| Zinc Oxide | 10% |
| Sulfur | 5% |
| Total | 100% |

Method of Preparation

The above mixture is ball-milled for a period of 6 hours and is then tested for particulate size to make certain the size is under 5 microns and then further milled for an additional period of time to ensure a particulate size of less than about 5 microns.

The mixture is then degassed as above and allowed to settle (about 6 or more hours) before packaging.

EXAMPLE 11

Scented Baby Powder Lotion

Materials: In Percent by Weight

Minor amount of dimethicone added for its known properties of lubricity and moisture retention.

| | |
|---|---|
| Cyclomethicone | 35% |
| Dimethicone | 4.5% |
| Starch | 60% |
| Scent | 0.5% |
| Total | 100% |

Method of Preparation

The above components are thoroughly mixed and the resulting mixture is slowly fed into a continuous-phase colloid mill with a mesh setting at 2-5 microns. A milling cycle of 2 hours is utilized and the resulting product is tested for particulate size. Milling is continued until all starch particles are within the 2-5 micron size range.

The above mixture is thereafter transferred into a closed chamber where it is degassed under vacuum for 2 hours and allowed to settle for an additional period of time (generally, about 10 hours) to produce the scented baby powder lotion.

EXAMPLE 12

Sore Muscle Rub Powder Lotion Containing Alcohol

Materials: In Percent by Weight

| | |
|---|---|
| Cyclomethicone | 30% |
| Starch | 55% |
| Menthol | 5% |
| Camphor | 5% |
| SD-40 Alcohol | 5% |
| Total | 100% |

Method of Preparation

The above components are thoroughly mixed and the resulting mixture is slowly fed into a continuous-phase colloid mill with a mesh setting at 2-5 microns. A milling cycle of 2 hours is utilized and the resulting product is tested for particulate size. Milling is continued until all starch particles are within the 2-5 micron size range.

The above mixture is thereafter transferred into a closed chamber where it is degassed under vacuum for about 2 hours and allowed to settle for an additional period to produce a liquid body powder.

EXAMPLE 13

Athlete's Foot Powder Lotion Containing Alcohol

Materials: In Percent by Weight

| | |
|---|---|
| Cyclomethicone | 25% |
| Starch | 40% |
| Sulfur | 10% |
| Isopropyl Alcohol | 10% |
| Zinc Oxide | 10% |
| Terconazole | 5% |
| Total | 100% |

Method of Preparation

The above components are thoroughly mixed and the resulting mixture is slowly fed into a continuous-phase colloid mill with a mesh setting at 2-5 microns. A milling cycle of 2 hours is utilized and the resulting product is tested for particulate size. Milling is continued until all starch particles are within the 2-5 micron size range.

The above mixture is thereafter transferred into a closed chamber where it is degassed under vacuum for about 2 hours and allowed to settle for an additional period of time to produce a liquid body powder.

EXAMPLE 14

Anti-Ache Powder Lotion Containing Alcohol

Materials: In Percent by Weight

| | | |
|---|---|---|
| Cyclomethicone | 30% | |
| Starch | 45% | |
| Sulfur | 15% | |
| Tetroquinone | 5% | |
| Isopropyl Alcohol | 5% | |
| Total | 100% | |

Method of Preparation

The above components are thoroughly mixed and the resulting mixture is slowly fed into a continuous-phase colloid mill with a mesh setting at 2-5 microns. A milling cycle of 2 hours is utilized and the resulting product is tested for particulate size. Milling is continued until all starch particles are within the 2-5 micron size range.

The above mixture is thereafter transferred into a closed chamber where it is degassed under vacuum for 2 hours and allowed to settle for an additional period of time to produce a liquid body powder.

EXAMPLE 15

Medicated Baby Powder Lotion Containing Alcohol

Materials: In Percent by Weight

| | | |
|---|---|---|
| Cyclomethicone | 35% | |
| Starch | 50% | |
| Zinc Oxide | 5% | |
| Sulfur | 5% | |
| SD-40 Alcohol | | |
| Total | 100% | |

Method of Preparation

The above mixture is ball-milled for a period of 6 hours and is then tested for particulate size to make certain the size is under 5 microns and then further milled for an additional period of time to ensure a particulate size of less than about 5 microns.

The mixture is then degassed as above and allowed to settle (about 6 or more hours) before packaging.

EXAMPLE 16

Evaporation Comparison of a Cyclomethicone Liquid Powder and a Dimethicone Liquid Powder The following liquid body powders are prepared utilizing cyclomethicone or alternatively, dimethicone to determine the effect that either delivery vehicle has on drying time. In each formulation, the amount of silicone fluid is 35% and the amount of starch is 65%.

Both formulations are prepared as described in Example 1, above.

The full evaporation time of the body powder containing cyclomethicone as the delivery vehicle on a glass plate is 10-12 minutes for a 5 mil thick film, leaving behind a pure coating of starch which was dry to the touch.

In comparison, the liquid powder containing dimethicone is spread onto a glass plate into a film having a thickness of 5 mil. The dimethicone does not evaporate leaving pure starch powder as is the case with the cyclomethicone, but instead the dimethicone containing liquid powder remained greasy to the touch indefinitely. The product remains on the skin as a greasy coating until wiped off. This is not viewed as a useful or viable product.

EXAMPLE 17

Evaporation Comparison of a Cyclomethicone Liquid Powder Containing Starch and a Cyclomethicone Liquid Powder Without Starch A number of liquid body powders were prepared utilizing cyclomethicone in combination with starch or alternatively, cyclomethicone alone to determine the effect that starch has on the drying time of cyclomethicone. In each formulation, the amount of silicone fluid was 35%, 50%, or 100% and the amount of starch ranged from 0% to about 50% by weight. Except as indicated, formulations containing the cyclomethicone (either decamethylcyclopentasiloxane "pentamer" or octamethylcyclotetrasiloxane "tetramer") and starch additives were prepared as described in the examples, above.

The following represents a comparison of cyclomethicone evaporation rates for liquid body powder formulations according to the present invention compared to pure cyclomethicone (containing no starch as evaporation enhancer or dispersant). In order to assess drying times, each of the following formulations with the exception of the composition containing 35% by weight octamethyltetrasiloxane, was placed into a chemical drying oven made by Chem-Dry. Samples weighing 500 mg of material were placed into a drying tube and left at 43° C. for a 6-hour evaporation interval in order to measure the evaporation rate of the cyclomethicone from each sample. Evaporation rates are calculated by calculating weight loss from each sample at the end of the six hour period. Evaporation rates were actually determined, or in the case of the 35% by weight tetramer-containing composition, extrapolated from existing data.

| Comparison of the Evaporation Rates of the Cyclomethicones With and Without Starch As Evaporation Enhancer/Dispersant | |
|---|---|
| Component Cyclosiloxane/Starch (Percent by Weight) | Evaporation Rate at 43° C. |
| Pentamer (no starch) | 3.4 mg/hr/cm$^2$ |
| Pentamer (50/50 with starch) | 5.2 mg/hr/cm$^2$ |
| Pentamer (35/65 with starch) | 12.8 mg/hr/cm$^2$ |
| Tetramer (no starch) | 14.0 mg/hr/cm$^2$ |
| Tetramer (50/50 with starch) | 22.1 mg/hr/cm$^2$ |
| Tetramer (35/65 with starch) | 32.0 mg/hr/cm$^2$* |

*Evaporation rate extrapolated from existing data.

As evidenced by the above experiment, the inclusion of starch increases the evaporation rate of volatile cyclomethicones used in the present invention by a factor of almost four, an unexpected result.

While there has been described what is considered to be preferred embodiments of the present invention, it will be readily apparent to those skilled in the art that modifications to the present invention can be made without departing from the scope of the teachings herein. As will be appreciated, such cyclic silicone fluids over time evaporate into pure silicone dioxide and carbon dioxide gases, which are completely non-toxic, completely inert, and provide substantially no negative byproducts. Although utilizing starch products produces a preferable product, other relative percentages and other polysaccharide dispersing powders may be employed, to essentially control the viscosity, rate of evaporation of the silicone fluid, and the amount of starch powder left behind. All of such choices are well within the skill of the routineer—and, for such reasons, resort should be had to the claims appended hereto for a true understanding of the scope of the invention.

I claim:

1. A talc-free liquid body powder composition consisting essentially of about 25% to about 75% by weight of a starch powder and about 25% to about 75% by weight of a volatile cyclomethicone mixed together to form a lotion or cream, said cyclomethicone in said composition, after application of said composition to a skin surface, evaporating to leave said starch powder on said skin surface.

2. The composition according to claim 1 wherein said starch powder is selected from corn starch or rice starch.

3. The composition according to claim 1, wherein said starch powder is milled to a particle size of less than about 10 microns.

4. The composition according to claim 1 wherein said starch powder is a pharmaceutical or food grade.

5. The composition according to claim 1 wherein said volatile cyclomethicone is selected from the group consisting of decamethylcyclopentasiloxane, octamethylcyclotetrasiloxane and mixtures thereof.

6. The composition according to claim 5 wherein said cylcomethicone is decamethylcyclopentasiloxane.

7. The composition according to claim 5 wherein said cyclomethicone is octamethylcyclotetrasiloxane.

8. The composition according to claim 1 wherein said starch powder comprises about 50% to about 75% by weight and said volatile cyclomethicone comprises about 25% to about 50% by weight.

9. The composition according to claim 1 wherein said starch powder and volatile cyclomethicone are mixed together in about equal amounts by weight.

10. The composition according to claim 1 including an effective amount of a medicinal selected from the group consisting of zinc oxide, sulfur, menthol, camphor, vitamin A, vitamin D, vitamin E or mixtures thereof.

11. The composition according to claim 1 further including an effective amount of an active agent selected from the group consisting of antifungal agents, antibiotics, anti-inflammatory agents, antipuritic agents, anti-acne agents, hemostatic agents, anti-histaminic agents and mixtures thereof.

12. The composition according to claim 1 further including an effective amount of an anti-fungal agent.

13. The composition according to claim 1 further including an effective amount of an anti-acne agent.

14. The composition according to claim 1 further including an effective amount of a film-former selected from petroleum jelly and mineral oil.

15. The composition according to claim 1 further including an effective amount of an antimicrobial agent.

16. The composition according to claim 1 further including an effective amount of an anti-inflammatory agent.

17. The composition according to claim 1 further including a volatile alcohol.

18. A liquid body powder consisting essentially of about 25% to about 75% by weight of a volatile cyclomethicone and about 25% to about 75% by weight of a starch powder mixed together to form a lotion or cream.

19. The composition according to claim 18 wherein said starch powder is selected from corn starch or rice starch.

20. The composition according to claim 18 wherein said starch powder is milled to a particle size of less than about 10 microns.

21. The composition according to claim 18 wherein said volatile cyclomethicone is selected from the group consisting of decamethylcyclopentasiloxane, octamethylcyclotetrasiloxane and mixtures thereof.

22. The composition according to claim 21 wherein said cyclomethicone is decamethylcyclopentasiloxane.

23. The composition according to claim 21 wherein said cyclomethicone is octamethylcyclotetrasiloxane.

24. The composition according to claim 18 wherein said starch powder comprises about 50% to about 75% by weight and said volatile cyclomethicone comprises about 25% to about 50% by weight.

25. The composition according to claim 24 further including a volatile alcohol.

* * * * *